United States Patent [19]

Henion et al.

[11] Patent Number: 4,935,624
[45] Date of Patent: Jun. 19, 1990

[54] THERMAL-ASSISTED ELECTROSPRAY INTERFACE (TAESI) FOR LC/MS

[75] Inventors: John D. Henion, Trumansburg; Edgar D. Lee; Thomas R. Covey, both of Ithaca, all of N.Y.

[73] Assignee: Cornell Research Foundation, Inc., Ithaca, N.Y.

[21] Appl. No.: 202,768

[22] Filed: Jun. 3, 1988

Related U.S. Application Data

[63] Continuation-in-part of Ser. No. 103,056, Sep. 30, 1987, Pat. No. 4,861,988.

[51] Int. Cl.$^5$ .............................................. H01J 49/10
[52] U.S. Cl. ..................................... 250/288; 250/281; 250/282
[58] Field of Search ................... 250/288, 288 A, 281, 250/282

[56] References Cited

U.S. PATENT DOCUMENTS

| | | | |
|---|---|---|---|
| 4,298,798 | 11/1981 | Takeuchi et al. | 250/288 A |
| 4,546,253 | 10/1985 | Tsuchiya et al. | 250/288 A |
| 4,730,111 | 3/1988 | Vestal et al. | 250/288 A |
| 4,794,252 | 12/1988 | Bateman et al. | 250/288 |

OTHER PUBLICATIONS

Fenn, J. B. et al., *Science*, 246:64–71, (1989).
Lee, E. et al., *J. Chromatogr*, 458:313, (1988).
Covey, T. R. et al., *Rapid Common. Mass Spectrom.*, 2:249, (1988).
Lee E. D. et al., *Journal of Microcolumn Separations*, 1:14, (1989).
Bruins, A. D. et al., *Anal. Chem.*, 59:2647, (1988).

*Primary Examiner*—Jack I. Berman
*Attorney, Agent, or Firm*—Jones, Tullar & Cooper

[57] ABSTRACT

A Thermal-Assisted Electrospray Interface (TAESI) used in series between a liquid chromatograph and a mass analyzer gives increased sensitivity for detection of components in a liquid stream at high flow rates up to 2 milliliters per minute. Liquid exiting the liquid chromatograph is sprayed through a stainless steel capillary tube while being heated externally and under an applied voltage of about 3 KV. The combination of thermal energy and electric field potential disperses the liquid into a fine mist which is then directed at atmospheric pressure into the ionization chamber of a mass spectrometer. Such a system, optionally may additionally contain a high velocity gas flow neubulization means.

The TAESI interface may be used without the electric field; however at flow rates of from 500 to 1000 $\mu$L/min the use of both electric field and thermal energy increases the sensitivity by two orders of magnitude over the interface used without the electric field.

24 Claims, 4 Drawing Sheets

ION SPRAY SIM FOR MULTIPLE INJECTIONS OF 500 NANOGRAMS OF ACID RED I (M/Z 464, 231)

THERMAL-ASSISTED ELECTROSPRAY SIM FOR MULTIPLE INJECTIONS OF 500 NANOGRAMS OF ACID RED I (M/Z 464, 231)

THERMAL-ASSISTED ELECTROSPRAY INTERFACE (TAESI) FOR LC/MS

This invention was at least in part funded under EPA Grant No. CR-811661-10-0; therefore, the Federal Government has certain rights in the invention.

FIELD OF THE INVENTION

This application is a continuation-in-part of co-pending application Ser. No. 103,056, filed Sept. 30, 1987, now U.S. Pat. No. 4,861,988, which is incorporated herein by reference.

This invention relates to method and apparatus for forming ions from a liquid, typically liquid from a liquid chromatograph (LC), and for directing such ions into a mass analyzer such as a mass spectrometer (MS).

More specifically the invention relates to an improved interface namely a thermally-assisted electrospray interface for LC/MS which accommodates high liquid flow rates at high sensitivity.

BACKGROUND OF THE INVENTION

Liquid chromatographs are commonly used for the separation of trace compounds to provide a degree of separation between the trace compound to be analyzed and the other compounds present in the mixture under investigation. The eluent from the liquid chromatograph, after the separation has occurred, is normally subjected to analysis to identify the trace compound or compounds of interest.

It is commonly desired to analyze the liquid from a liquid chromatograph in a mass analyzer such as a mass spectrometer. However, since mass spectrometers require an input in the form of free ions, it is usually necessary to evaporate the liquid from the liquid chromatograph, and to produce ions during or after the vaporization process.

One classical method which was commonly used was to spray the liquid from the liquid chromatograph onto a moving belt, which moves into a vacuum chamber where the belt was heated from below. The resultant vapor was then ionized by appropriate means. Another classical method was to spray large droplets from the liquid chromatograph into a heated ion source, so that the droplets were vaporized (typically by contact with the walls of the ion source and by exposure to the instrument vacuum). Both these methods use substantial heat, and this has severe disadvantages. The heat causes thermal decomposition of the compounds in question, and in addition, since the liquid from the liquid chromatograph often contains ammonium ions, these ions often cause ammonium chemical ionization to occur. The thermal decomposition and the ammonium chemical ionization create complexity in the final mass spectrum, making the analysis process more difficult.

More recently three alternative methods have been developed for introducing the liquid from a liquid chromatograph into a mass analyzer. In one method, referred to as ion evaporation, liquid is sprayed at atmospheric pressure into a chamber in front of the vacuum chamber orifice for the mass analyzer. The spray is directed across the orifice into a 90 degree elbow tube. This removes large droplets. The finer portion of the spray is removed less quickly, and since the small droplets therein carry a charge impressed by an electric field which is applied between the sprayer and an induction electrode, ions are released therefrom as the droplets evaporate. Such ions are driven toward the orifice by a deflector electrode. Although this method can accommodate relatively high flows (e.g. 1 milliliter per minute), the method is not particularly sensitive, partly because much of the sample is unused. Thus, the ion current from compounds of interest is very low in this method.

The second relatively modern method which has been developed is referred to as thermospray. In this method, the flow of liquid from the conventional liquid chromatograph passes through a capillary, the end of which is heated to between 200 and 350 degrees C. The resultant vaporization results in a spraying process, which is usually into a low pressure chamber but can be into an atmospheric pressure chamber. Contrary to the ion evaporation process, the droplets formed are charged not by an electric field, but rather by statistical fluctuations in the distribution of ions in solution when the liquid is dispersed into an aerosol. As the charged droplets evaporate, ions are released therefrom. Thermospray is relatively effective in producing a fine mist and currently is commonly used. However, a substantial disadvantage of the process is that again, some thermal decomposition occurs, even though not all of the liquid is directly subjected to heating. In addition, again some unwanted ammonium chemical ionization may occur. Therefore, while the temperatures used can be carefully controlled by a microprocessor, nevertheless, thermospray is commonly recognized as being a "fussy" process which may give good results one day and poor results another. In addition, in practice some workers report that thermospray is generally less sensitive for ionic compounds (i.e. compounds which form ions in solution) than is the ion spray technique.

The third process which has been used to produce ions from the liquid of a small-bore liquid chromatograph, and to introduce such ions into a mass analyzer, is the so-called electrospray technique. In this technique, liquid from the liquid chromatograph is directed through a capillary tube the end of which is connected to one pole of a high voltage source. The end of the capillary tube is spaced from the orifice plate through which ions travel into the mass analyzer vacuum chamber. The orifice plate is connected to the other pole of the high voltage source. The electric field generates charged droplets, producing an induced liquid flow in the capillary without a pump, and the droplets evaporate to produce ions. Electrospray can be carried out without a pump (in which case the flow is 1 to 2 microliters per minute) or with a pump.

The electrospray method has several disadvantages. Firstly, it can handle only a very small flow, typically only up to about 10 microliters per minute. Faster pumping produces larger droplets, causing the ion signal to fall off and also to become unstable. Secondly, the high voltages needed to disperse a larger liquid flow into fine droplets tend to create an electrical or corona discharge. The discharge adds complexity to the spectrum produced by the mass analyzer, causing difficulties in interpretation, and in addition, for unknown reasons, it tends to suppress the ion signal from the evaporated droplets. A further disadvantage is that the electrospray method is very sensitive to the position of the end of the capillary tube relative to the orifice plate.

In addition, the electrospray method requires that the proportion of water in the liquid be low, since otherwise a stream of large droplets tends to be produced. The large droplets reduce the sensitivity (i.e. the ion signal) and also affect the stability of the ion signal, i.e. large fluctuations occur in the ion signal.

Prior Electrospray (ES) apparatus and ion spray (IS) apparatus and methods of interfacing liquid chromatographs with a mass analyzer including U.S. Pat. No. 4,861,988 relating to "Ion Spray Apparatus and Method" are deficient in the amount of liquid that can be accommodated in the interface without loss of sensitivity and selectivity. Prior art Electrospray interfaces only accommodate liquid flow rates of from about 1.0 to 10 µL per minute. It would be advantageous to have interfaces that would operate with high sensitivity at flow rates of from 100 µL up to 1000 µL–2000 µL/minute. Known Electrospray and Ion Spray interfaces suffer also from the fact that they produce a high abundance of multiply charged ions which detract from the identification of unknown chemicals by their mass spectra. It would be further advantageous to have an interface that predominately generates singly charged ions.

The present invention resolves the various deficiencies of the prior art interfaces.

SUMMARY OF THE INVENTION

Figure 1:
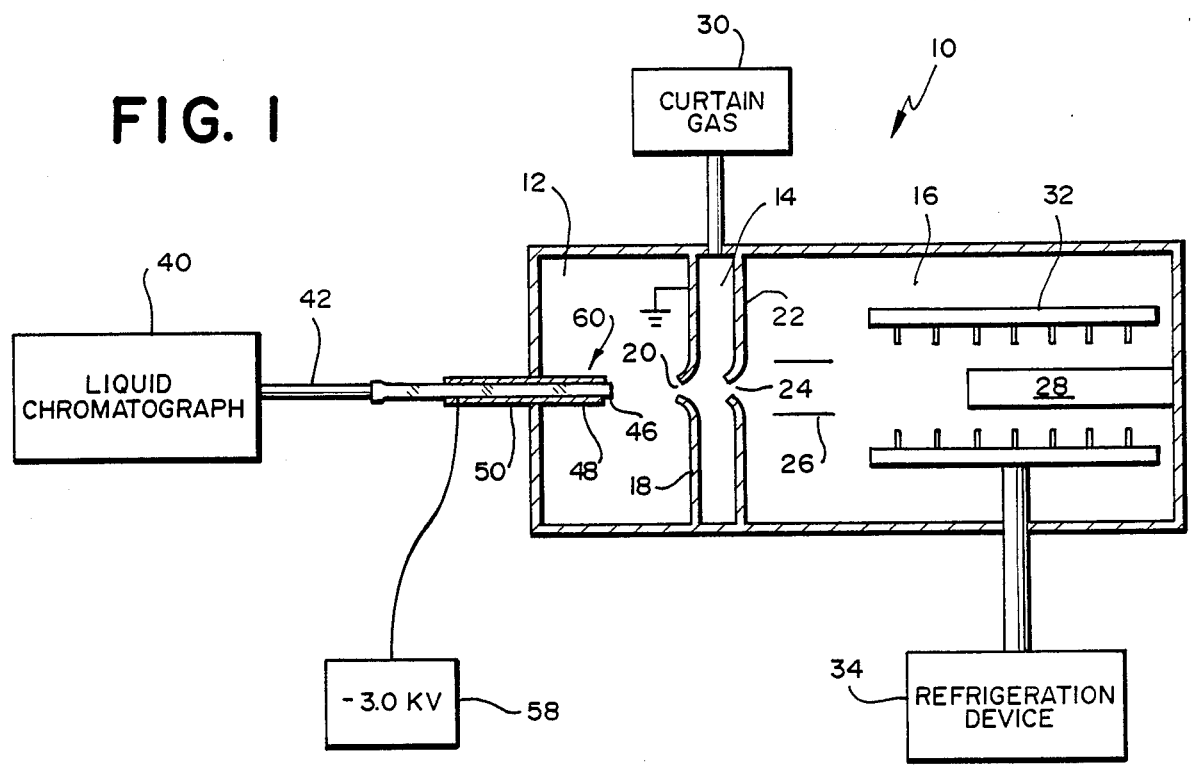
FIG. 1 is a diagrammatic view of apparatus according to the invention showing the thermal-assisted electrospray in series between the liquid chromatograph and the mass spectrometer.

The invention in one of its aspects provides improved apparatus for forming ions predominantly singly-charged ions at atmospheric pressure from a liquid and for introducing such ions into a mass analyzer. In its broadest aspect the present invention provides apparatus for forming ions from a liquid having high flow rates of up to about 2000 µL/minute and for introducing said ions into a mass analyzer, comprising:

(a) a conductive capillary tube to receive said liquid and having a first free end;

(b) a thermal energy means for directly or indirectly heating the liquid in the capillary tube;

(c) optionally an outer tube encircling said inner capillary and defining therewith a narrow annular space there-between, said outer tube having a second free end located substantially at said first free end, (d) an orifice plate having an orifice therein, said capillary tube and optional outer tube being located on one side of said orifice plate with said free ends spaced therefrom, (e) a mass analyzer on the other side of said orifice plate for receiving ions passing through said orifice plate, (f) and means for generating an electric field between said first free end and said orifice plate, whereby the combination of said thermal energy and said electric field applied to the liquid emerging from the free end of the capillary tube and optional gas flow past said free end of said inner conductive tube produces a mist of fine charged droplets of said liquid, so that said charged droplets may evaporate and release ions therefrom; said droplets having a predominance of singly-charged ions relative to multiply-charged ions and having a single polarity, either positive or negative, the same as the polarity of the applied electric field, (g) optional means for directing a flow of gas through said annular space at a high velocity.

In another aspect, the invention provides a method of forming ions at atmospheric pressure from a liquid and for introducing said ions into a mass analyzer, comprising:

(a) directing said liquid through a conductive capillary tube having a free end, (b) heating said liquid and optionally directing a high velocity annular jet of inert gas past said free end in the direction of flow of said liquid, (c) generating an electric field between said free end and an orifice plate for said ions, the combination of said heating and said electric field, optionally under said annular jet of gas, acting to produce a mist of charged droplets and to produce ions from said droplets; said droplets having a predominance of singly-charged ions relative to multiply-charged ions and having a single polarity, either positive or negative, corresponding to the polarity of the applied electric field; and (d) guiding said ions through said orifice into a mass analyzer located beyond said orifice.

Another aspect is the above-described thermally-assisted electrospray interface apparatus which forms ions for detection by a mass spectrometer wherein the singly-charged ions of one polarity are generated by treating a high flow rate liquid with a combination of thermal energy and an electric field wherein the thermal energy is selected from the group consisting of electrically resistive heating, piezoelectric heating, ultrasonic heating, infrared heating, microwave heating, and conductive from gas heating: Electrically resistive heating is preferred.

Yet another aspect is a thermally-assisted electrospray interface apparatus as discussed herein wherein a liquid heated in a capillary tube and under the influence of an applied electric field exits the capillary tube predominantly as singly-charged ions which are directed toward an orifice plate 18, wherein said tube is positioned parallel to said orifice plate.

Further objects and advantages of the invention will appear from the following description, taken together with the accompanying drawings.

DETAILED DESCRIPTION OF PREFERRED EMBODIMENT

Reference is made to FIGS. 1, 2, 3 and 4 which shows diagrammatically at 10 a typical mass spectrometer instrument used in series with a liquid chromatograph 40 and a thermally assisted electrospray interface 46. The instrument 10 is typically that sold by Sciex Division of MDS Health Group Limited of Thornhill, Ontario, Canada, under its trade mark TAGA 6000E. The instrument 10 includes an atmospheric pressure ionization chamber 12, a gas curtain chamber 14 and a vacuum chamber 16. The ionization chamber 12 is separated from the gas curtain chamber 14 by an inlet plate 18 containing an inlet orifice 20. The gas curtain chamber 14 is separated from the vacuum chamber 16 by an orifice plate 22 containing an orifice 24.

In use, the sample to be analysed is introduced into the ionization chamber 12 and is ionized as will be described. The ions are drawn by an electric field through the inlet opening 20, through the orifice 24, and are focused by a lens 26 into a tandem triple quadrupole mass spectrometer 28.

In order to prevent gases from the ionization chamber 12 from entering the vacuum chamber 16, the gas curtain chamber 14 is supplied from a source 30 with a curtain gas (typically nitrogen or argon) at a pressure higher than that prevailing in the ionization chamber 12. Gas from the gas curtain chamber effuses through the orifice 20 into the ionization chamber 12 and also passes through the orifice 24 into the vacuum chamber 16. In the TAGA instrument described, the vacuum is produced by cryopumping, i.e. the nitrogen, argon or other curtain gas is condensed on cooling fins 32 which are cooled by a refrigeration device 34.

Figure 2:
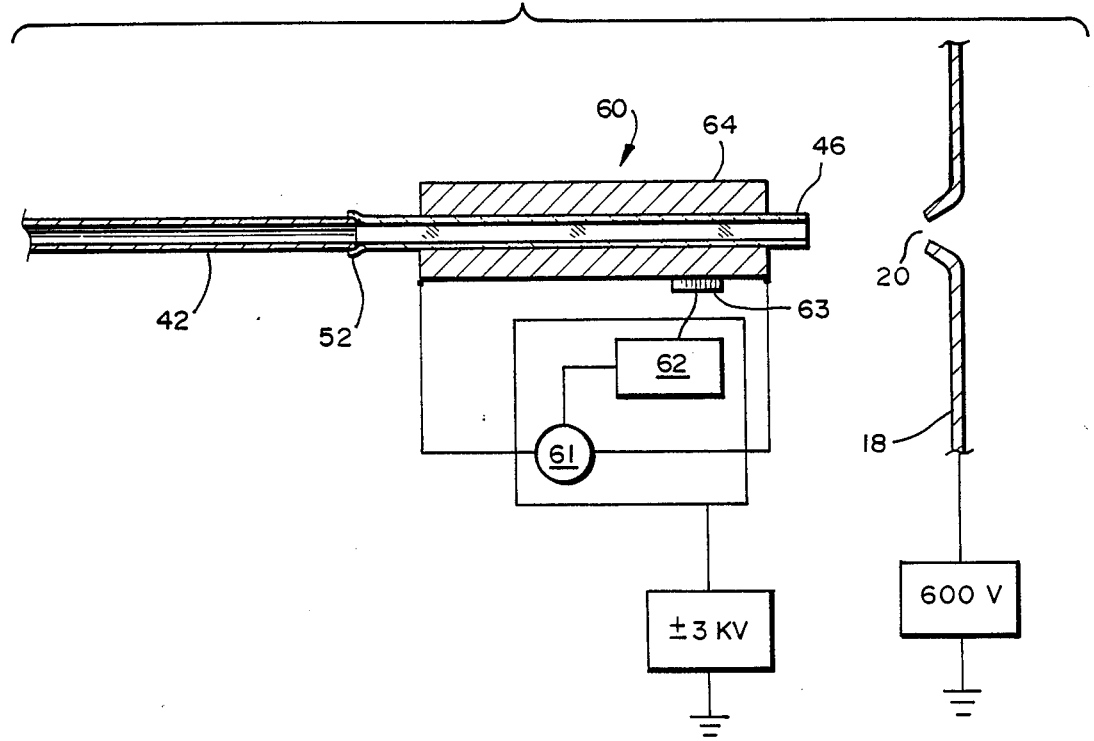
FIG. 2 is a diagrammatic view of the thermally assisted electrospray interface showing a capillary tube 46 with resistive heating means and sheath used in the FIG. 1 apparatus.
Figure 3:
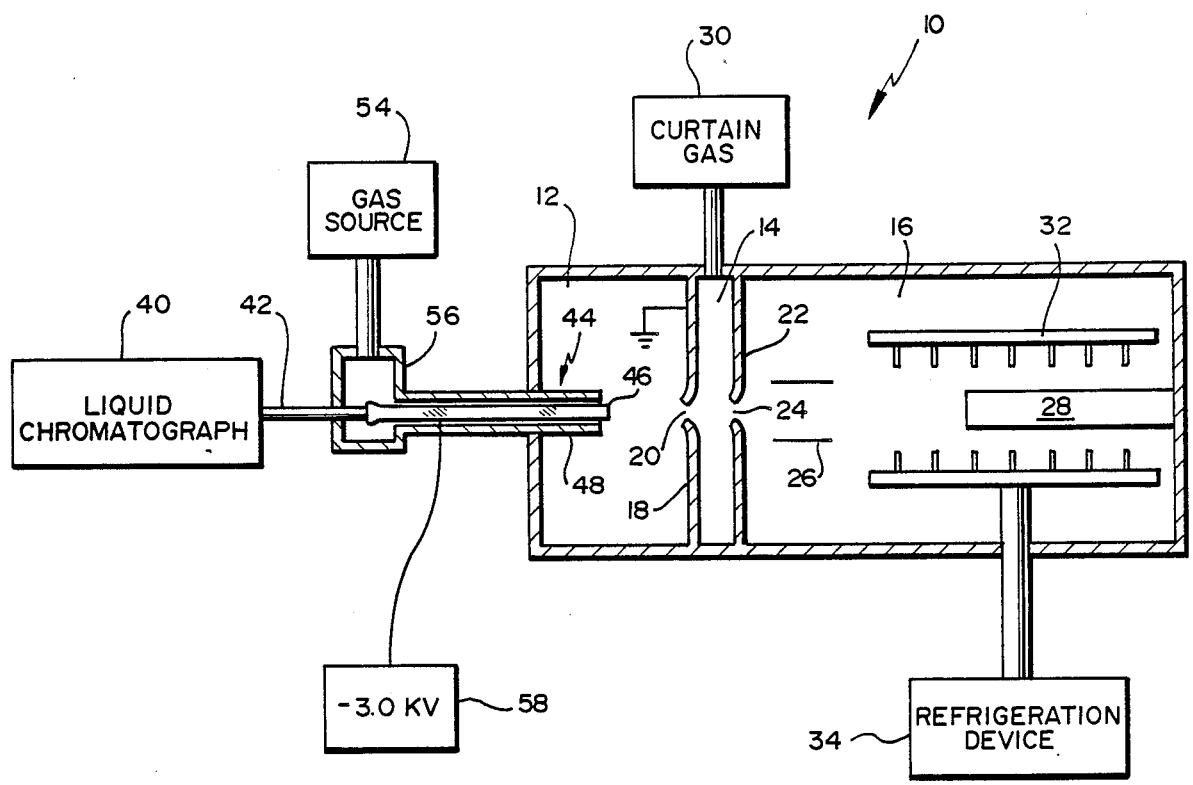
FIG. 3 is a diagrammatic view of the thermally assisted electrospray interface used in series between the chromatograph and mass detector as adapted for the optional use of the high velocity annular gas flow in the outer tube 48 encircling the inner capillary tube.

The thermal-assisted interface (TAESI) of the present invention include various modifications. One form of the interface is shown in FIG. 2. Referring to FIG. 2, the capillary tube 46 is enclosed within heater tube 64 which is directly heated by a low voltage high current power supply 61 using feedback controller 62 to regulate the power supply 61. The temperature of the heater tube 64 is controlled by thermocouple 63 in the temperature range of about 150° C. to about 170° C. The temperature of the liquid (aerosol jet droplets) exiting the capillary tube is maintained at a temperature below about 150° C., preferably below 100° C. and most preferably at about 20° C. to about 75° C. Such temperatures are achieved even though the temperature of the heater tube 64 surrounding the capillary tube 46 is maintained at about 170° C. by thermocouple 63. The low temperature of the exiting droplets is a critical aspect of the present invention in preventing the thermal decomposition of components inherent in prior electrospray and ion spray apparatus. It is preferred to heat the heater tube 64 which is in contact with the capillary tube 46. Alternatively the capillary tube may be heated directly or indirectly.

While the preferred means for heating the liquid passing through the capillary tube is by electric resistive heating, the TAESI interface is not limited thereto. One skilled in the art will recognize other means for heating the liquid within the capillary tube which when combined with the electric field means gives the improved ions for increased sensitivity. These include for example piezoelectric heating, microwave heating, ultrasonic heating, infrared heating and heating by conductive gas used in the gas flow nebulization means, when applicable. Thus, with other heating modes, the conductive capillary tubing can be substituted with capillary tubing suitable for such other heating modes. For example, plastic tubing or glass tubing would suffice for systems using microwave heating.

Figure 4:
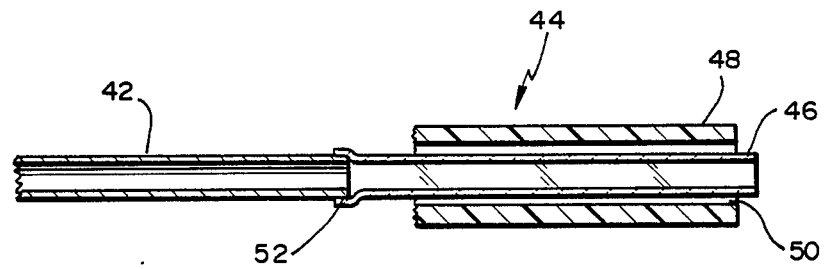
FIG. 4 is a diagrammatic view of the interface adapted for optional use of the high velocity annular gas flow in the outer tube 48 encircling the inner capillary tube 46.

According to the invention, liquid from a liquid chromatograph 40 or fluid from a fluid chromatograph flows through a thin quartz tube 42 into a device 60 shown in FIG. 2 and which will be referred to as a "heated electrospray" device. The heated electrospray device 60 comprises a stainless steel capillary tube 46 of circular cross-section, optionally encircled by an outer tube 48 (FIG. 4) also of circular cross-section. The inner diameter of the stainless steel capillary tube 46 is typically 0.1 millimeters, and its outer diameter is typically 0.2 millimeters. The inner diameter of the optional outer tube 48 shown in FIG. 4 is typically 0.25 millimeters, leaving an annular space 50 between the two tubes of thickness 0.025 mm. The outer diameter of the outer tube 48 is not critical and the outer tube 48 can be made of any desired thickness depending on the material from which it is formed. Normally, the tip of the stainless steel tube 46 protrudes slightly from the outer tube 48.

Typically the quartz tube 42 from the liquid chromatograph 40 will be 0.050 mm inner diameter. The tube 42 is sealed at its end 52 to the stainless steel tube 46, so that the liquid or fluid flowing in the tube 42 can expand into the stainless steel tube. The stainless steel tube 46 is typically about 10 centimeters in length, although this may vary.

A source 58 of electric potential can be connected either to the stainless steel tube 46 or to the heater tube 64 as shown in FIG. 2. For negative ion operation, the stainless steel capillary may be kept at −3000 volts, and for positive ion operation at +3000 volts. The orifice plate 18 is floated at ±600 V.

A further modification which includes a gas nebulization means with heating means and electric field means is shown diagrammatically in FIG. 4. In FIG. 4, the heating means is not shown; heating means can be of the same type as used in FIG. 2. In this mode, when the interface apparatus includes optional tube 48, a gas, typically nitrogen boiled from liquid nitrogen, is introduced into space 50 between the tubes 46, 48 from a gas source which is connected to the outer tube 48 by a fitting through which the conductive capillary tube 46 passes. Other gases, such as "zero air" (i.e. air with no moisture) or oxygen can also be used. Nitrogen from gas source 54 can be supplied at a pressure of from 2.0 to 4.0 bar (i.e. 2.5–4 atmospheres) into the annular space 50. This produces a high gas velocity through the space 50, namely, a velocity of gas in the range between about 140 to 250 meter per second.

During normal operation, the axis of the stainless steel tube 46 was positioned 5 to 10 millimeters off the axis of the orifices 20, 24, to prevent sampling of large cluster ions. A fine mist or fog was observed emanating from the tip of the tube 46. It was found that the combination of the electric field and the heat served to nebulize the liquid stream. The device shown was tested and found effective at flow rates from about 100 μL/min to 2000 μL/minute. The best sensitivity was obtained at about 500 microliters per minute, a flow rate which is compatible with 4.6 millimeter inner diameter packed liquid chromatograph columns. It was also found that the best sensitivity was achieved when the tip of the stainless steel tube 46 was positioned one to two centimeters from the orifice plate 18. However, the spray process was relatively independent of the position of the tip of tube 46. Alternatively the tip of the capillary tube can be positioned at 90° relative to the axis of the orifice plate 18. In such case the stainless steel tube 46 is positioned parallel to the orifice plate 18. Improved sensitivities and lower chemical background signals are obtained with this configuration. Tube 46 is positioned about 1-2 cm from orifice plate 18 and the end of tube 46 is positioned 0.5 to 2 cm from orifice 20.

It will be appreciated that the invention is applicable only for certain compounds. It is primarily applicable for ionic compounds, i.e. compounds which are already ionized in solution. These compounds include many dyes and drugs. In addition, the method is applicable in the case of certain neutral molecules which associate with ions in solution and remain associated with the ions during the thermally-assisted electrospray process. Examples of such compounds having neutral molecules which cluster with ions are digitoxin and certain estrogens, e.g. diethyl stilbestrol.

The invention has been tested on members of a number of classes of compounds which, when present in very small quantities (and since they are usually accompanied by other compounds) have heretofore proven very difficult to detect reliably. The application has performed surprisingly well on various members of the following classes of compounds:
1. disulfonated azo dyes
2. phenolic compounds
3. carboxylic acids
4. various fragile drug compounds (e.g. digitoxin as mentioned, nystatin, and a drug produced by Squibb under its trademark Aztreonam
5. nucleotides
6. glycol polymers It is found that the use of the invention produces mild ionization, particularly ions that are predominantly singly charged and accommodates large samples (total output) from the liquid or fluid chromatograph and does so at very high sensitivity. Surprisingly good results obtain even when very small quantities of many compounds which are difficult to detect are involved.

Figure 6A:
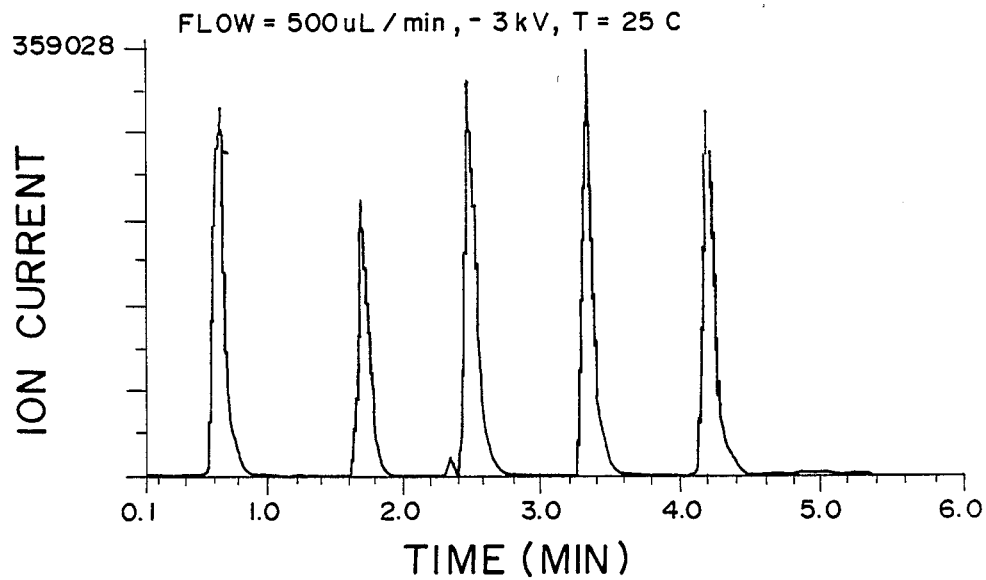
FIGS. 6A and 6B are ion current (ion current v. time) chromatograms (selected ion monitoring, SIM) comparing (A) ion spray multiple injections of a test sample (Acid Red 1) with (B) thermal-assisted electrospray showing a three-fold increase in sensitivity for (B) using a liquid flow rate of 500 µL/minute, a heater tube temperature of 170° C. and an applied field of −3 kV.
Figure 6B:
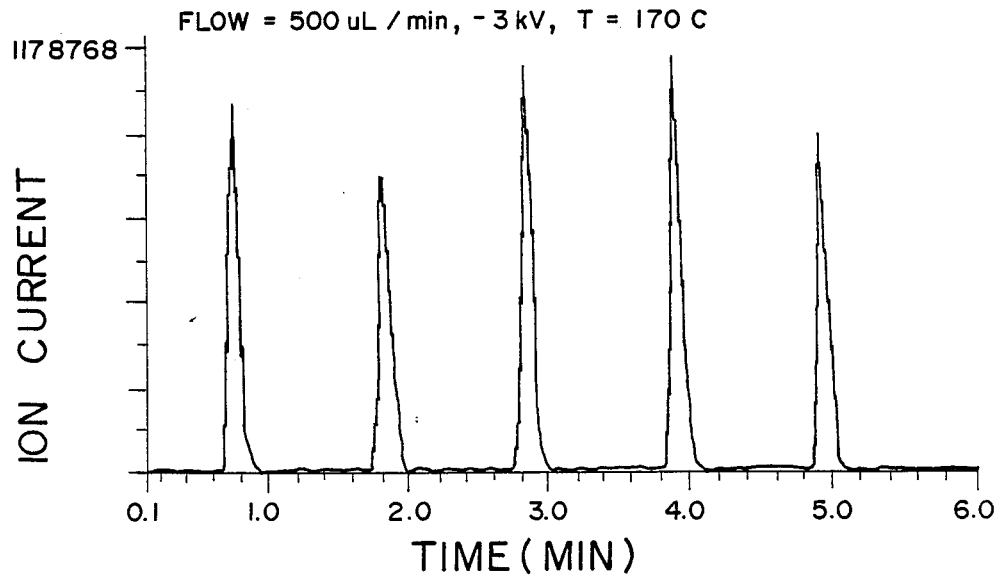

When the liquid flow rates are raised to the 100–1000 $\mu L$/minute range with the pneumatically nebulized ion spray device as shown in U.S. Pat. No. 4,861,988, ion current signal drops significantly. It is believed that this is due to the presence of large droplets which are not dispersed or broken up by the gas stream. By the addition of heat as an external energy source to the conductive capillary, significant gains in sensitivity can be achieved, as shown in FIGS. 6A and 6B. In the experiment shown in FIG. 6A, ion spray, representative of that shown in co-pending application Ser. No. 103,056, was operated at 500 $\mu L$/min flows and the signal from the test compound (Acid Red 1) is shown to be lower by a factor of 3 than the signal in FIG. 6B where the capillary tube 46 is heated by resistive heating while subjected to an electric field (applied voltage of about 2400 V). Acid Red #1 is a disulfonated azo dye.

Figure 5A:
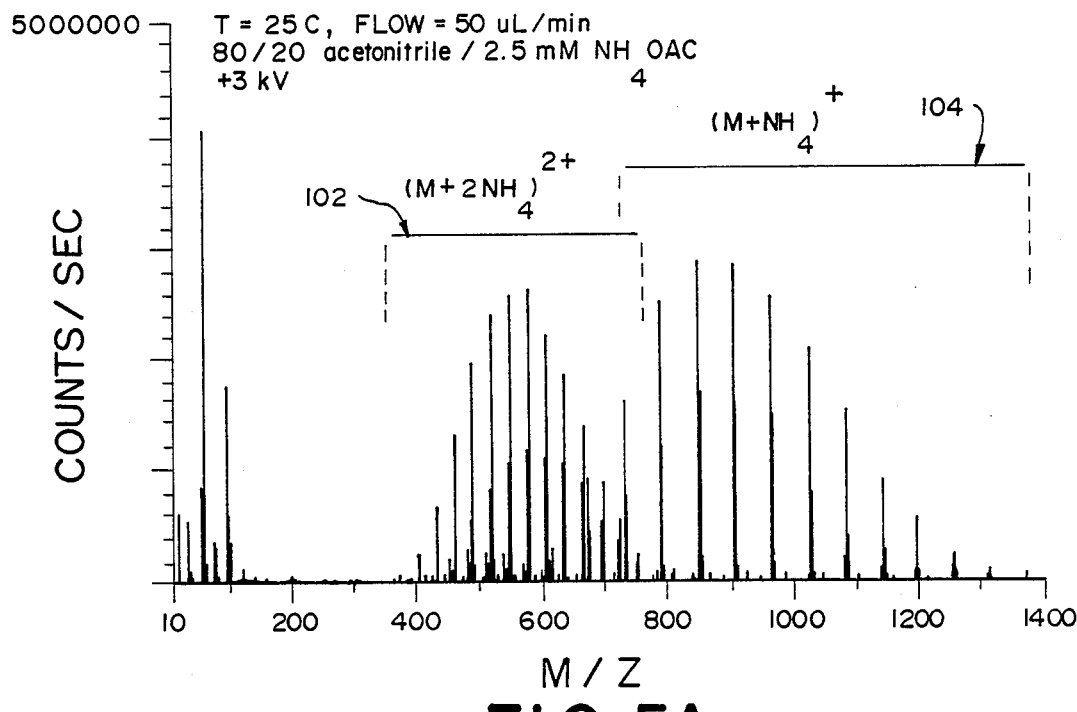
FIGS. 5A and 5B are mass spectra for polypropylene glycol 1000 comparing (A) ion spray interface with (B) thermal-assisted electrospray showing relative amounts of singly-charged and doubly-charged species at flow rates of 50 µL/minute and 500 µL/minute respectively.
Figure 5B:
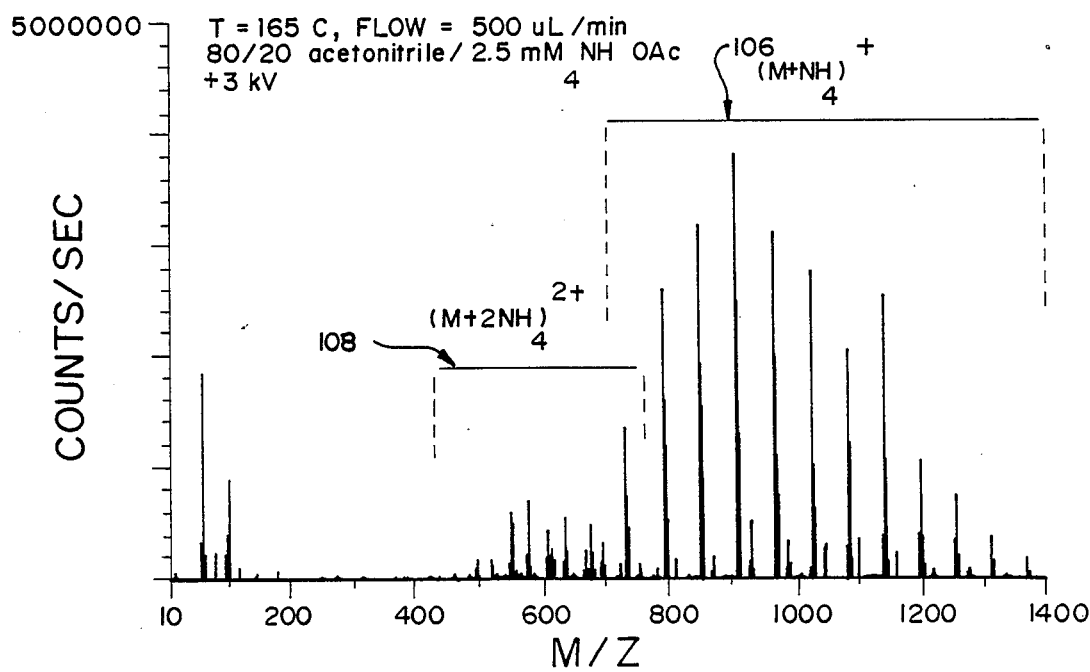

A second beneficial effect is achieved when thermal energy is applied to the liquid; the ions formed from unfragmented molecular species are predominately of the singly charged nature which directly corresponds to the molecular weight of the molecules. Without heat multiply-charged species form in high abundance which complicates the interpretation of the spectrum. FIG. 5A shows the ion spray mass spectra of polyproplyene glycol 1000 test sample as having highly abundant doubly-charged species indicated by reference numeral 102. These are nearly as abundant as the singly-charged species 104. FIG. 5B shows the situation where heat is applied to the liquid by direct electrical heating of the capillary tube. The singly charged molecular ions reference 106 of the polyproplyene glycol polymers has increased slightly while the multiply-charged ions, reference 108, was substantially reduced.

Had the electric field applied been higher (by using higher voltage or by moving the tip of tube 46 closer to plate 18), the ion signal would have been greater at lower pressures. However too high an electric field creates a risk of creating a corona discharge.

The inner diameter of the capillary tube 46 may vary, depending on the application. A diameter of 100 microns (a micron is 0.001 mm) was found suitable. Typically, the inner diameter may range between 25 and 250 microns. In addition, the thickness of the annular space 50 may vary, a preferred thickness being 75 microns.

While the description shows the liquid or fluid flow into the thermal-assisted electrospray device 60 as being from a liquid or fluid chromatograph, in suitable circumstances the liquid flow can be injected directly into the thermal assisted electrospray device 60 without a liquid chromatograph column.

It is noted that a high percentage of methanol or acetonitrile in the liquid directed into tube 46 helps the pneumatic dispersion into droplets small enough for the emission of ions. Methanol and acetonitrile have a lower dielectric constant than water and hence allows ions to escape more readily. The presence of ammonium acetate (a common buffer salt) at a concentration of 0.01 M and above strongly reduced the sensitivity for ionic analytes. However, the same concentration of ammonium hydroxide or acetic acid did not have this adverse effect.

It is noted that a high percentage of water in the eluent or sample solution did not impair the performance of the thermal-assisted electrospray interface in the tests which were conducted, contrary to the case of the prior art electrospray interface.

The increase in sensitivity for the thermal-assisted electrospray interface of the present invention is shown in FIGS. 6A and 6B. Ion current density (plot of ion current v. time) chromatograms (selected ion monitoring, SIM) for (A) ion spray multiple injections of a test sample (Acid Red 1) is directly compared with (B) thermal assisted electrospray. The thermal assisted electrospray interface gives a three-fold increase in sensitivity using a liquid flow rate of 500 $\mu L$/minute, a temperature of 170° C. at the thermocouple 63 of FIG. 2 under an applied field of $-3$ kV when compared with an ion spray interface (SIM) at a flow rate of 500 $\mu L$/minute, an applied field of $-3$ kV and a temperature of 25° C.

The temperature of the liquid exiting the capillary tube of the thermal-assisted electrospray interface is less than about 100° C. even though the thermocouple and heated tube is at a higher temperature.

The mass spectrometer used for these experiments was a Sciex TAGA 6000E equipped with an atmospheric pressure ion source. The pneumatic assisted electrospray interface used was the ion spray LC/MS interface. The thermal assisted electrospray interface was constructed from a 250 $\mu m$ i.d. $\times$ 1.6 mm o.d. $\times$ 10 $\mu m$ stainless steel tube which was heated by a direct AC current, applying approximately 50 watts of energy with a 3-5 volt potential. A 200 $\mu m$ o.d. $\times$ 100 $\mu m$ i.d. stainless steel capillary was fed through the stainless steel tube. The end of the capillary extended 0.3 cm beyond the end of the thermospray probe for the electrospray needle necessary to create a high electric field for nebulization. The probe and power supply were floated at a ±3 kV electrospray potential.

The term "liquid" as used in this invention refers to liquid in its normal sense as well as to a compressed gas or liquid delivered as a fluid as from a chromatographic system. One example of a useful fluid is carbon dioxide as typically used in supercritical fluid chromatography (SFC).

What is claimed is:

1. Apparatus for forming ions at atmospheric pressure from trace sample molecules in a liquid and for introducing said ions into a mass analyzer, comprising:
   (a) a chamber,
   (b) a conductive capillary tube to receive said liquid and having a first free end within said chamber,
   (c) a thermal energy means for heating the liquid in the tube said thermal energy means extending substantially the length of the tube within the chamber,
   (d) an orifice plate having an orifice therein, said tube being located on one side of said orifice plate in said chamber with said free end spaced therefrom said orifice defining an outlet from said chamber,
   (e) a mass analyzer on the other side of said orifice plate, outside said chamber for receiving ions passing through said orifice plate,
   (f) and means for generating an electronic field between said first free end and said orifice plate,
   (g) the pressure in said chamber being substantially atmospheric pressure,
   wherein the combination of said thermal energy and said electric field applied to liquid merging from the free end of said conductive tube produces a mist of finely charged droplets of said liquid so that said charged droplets evaporate in said chamber and release ions therefrom; said droplets having a predominance of singly charged ions relative to multiply charged ions and having a single polarity, either positive or negative, the same as the polarity of the applied electric field.

2. Apparatus according to claim 1 wherein said capillary tube is formed from an electrically conductive material and is positioned accept a liquid flow rate of liquid passing the tube at a flow rate of from about 100 μL/min to about 2000 μL/minute; said electric field generating means sufficient to provide an electric field of up to about 3 kV; and a thermal energy means sufficient to generate a temperature at the first free end of said capillary tube of from about 20° C. to 150° C.

3. Apparatus according to claim 2 wherein said capillary tube is a stainless steel tube and said means for generating said electrical field includes means for applying a potential to said stainless steel tube.

4. Apparatus according to claim 2 wherein the inner diameter of said capillary tube is between from about 0.025 to 0.20 millimeters.

5. Apparatus according to claim 4 wherein the inner diameter of said capillary tube is of the order of 0.1 millimeters.

6. Apparatus according to claim 4 wherein said thermal energy means applied to the liquid is selected from the group consisting of (1) electrically resistive heating (2) piezoelectric heating (3) ultrasonic heating (4) infrared heating and conductive from gas heating.

7. Apparatus according to claim 6 wherein said thermal energy means is electrical resistant heating.

8. The apparatus according to claim 7 wherein the temperature of the liquid at the first free end of said capillary tube is less than about 100° C.

9. Apparatus according to claim 2 and including a liquid chromatograph for supplying said liquid, said liquid chromatograph having an outlet tube for said liquid flowing therefrom, said outlet tube being of an insulating material and being connected to said inner tube for said inner tube to receive the entire flow from said liquid chromatograph.

10. A method of forming ions in a chamber at atmospheric pressure from trace sample molecules in a liquid and for introducing said ions into a mass analyzer, comprising:
   (a) directing said liquid through a conductive capillary tube having a free end to produce a aerosol jet of droplets emerging at said free end in said chamber;
   (b) heating the liquid in the capillary tube by applying heat substantially over the length of the tube within said chamber;
   (c) maintaining the pressure in said chamber at substantially atmospheric pressure;
   (d) applying an electric field between said free end and an orifice plate for said ions, the combination of said heating and said electric field acting to produce a mist of charged droplets and to produce ions in said chamber from said droplets; said charged droplets having a predominance of singly charged ions relative to multiply-charged ions and having a single polarity, either positive or negative, the same as the polarity of the applied electric field; and
   (e) guiding said ions out of said chamber through an orifice in said orifice plate into a mass analyzer located outside said chamber beyond said orifice plate.

11. The method according to claim 10 wherein the temperature of the aerosol jet is from about 20° C. to 150° C. and the flow rate of the liquid entering the capillary tube is from about 100 μL/minute to 2000 μL/minute.

12. The method of claim 11 wherein the temperature of the aerosol jet is less than 100° C. and the liquid flow rate is from about 500 to 1000 μ/L minute.

13. Apparatus for forming ions at atmospheric pressure from trace sample molecules in a liquid and for introducing said ions into a mass analyzer, comprising:
   (a) a chamber;
   (b) a conductive capillary tube to receive said liquid and having a first free end within said chamber;
   (c) a thermal energy means for heating the liquid in the tube;
   (d) a gas flow nebulization means which comprises:
      (1) an outer tube encircling said conductive capillary and defining therewith a narrow annular space therebetween, said outer tube having a second free end located substantially at said first free end, said second free end also being in said chamber, and
      (b 2) means for directing a flow of gas through said annular space in the direction of the liquid flow for said gas to flow over said first free end into said chamber at a velocity sufficient to nebulize said liquid;
   (e) an orifice plate having an orifice therein, said capillary tube being located on one side of said orifice plate with said free end spaced therefrom, said orifice defining an outlet from said chamber;

(f) a mass analyzer on the other side of said orifice plate outside said chamber for receiving ions passing through said orifice plate, and (g) means for generating an electric field between said first free end and said orifice plate; wherein the pressure in said chamber is substantially atmospheric pressure and wherein the combination of said thermal energy, said electric field and said nebulization produces a mist of finely charged droplets of said liquid so that said charged droplets evaporate in said chamber and release ions therefrom; said droplets having a predominance of singly charged ions relative to multiply charged ions and having a single polarity.

14. Apparatus according to claim 13 wherein the thickness of said annular space is of the order of 0.075 millimeters.

15. Apparatus according to claim 13 wherein said means for directing said flow of gas includes a source of pressurized gas, the pressure of said gas being between 2 and 3 bar.

16. Apparatus according to claim 15 and including a liquid chromatograph for supplying said liquid, said liquid chromatograph having an outlet tube for said liquid flowing therefrom, said outlet tube being of an insulating material and being connected to said tube for said capillary tube to receive the entire flow from said liquid chromatograph.

17. Apparatus according to claim 16 wherein said gas is nitrogen.

18. Apparatus according to claim 13 wherein said first free end of the capillary tube extends slightly beyond said second free end.

19. Apparatus according to claim 13 wherein said nebulization means includes means for producing a gas velocity of between about 140 and 250 meters per second through said annular space.

20. Apparatus according to claim 13 wherein said capillary tube is formed from an electrically conductive material and is adapted to accept a liquid flow rate of liquid passing the tube at a flow rate of from about 100 $\mu$L/min to about 2000 $\mu$L/minute; said electric field generating means sufficient to provide an electric field of up to about 3 kV; and a thermal energy means sufficient to generate a temperature at the first free end of said capillary tube of from about 20° C. to 150° C.

21. A method of forming in a chamber at atmospheric pressure ions from trace sample molecules in a liquid and for introducing said ions into a mass analyzer, comprising:

(a) directing said liquid through a conductive capillary tube having a free end to produce an aerosol jet of droplets emerging at said free end in said chamber;

(b) heating the capillary tube within the chamber at a temperature sufficient to maintain the temperature of said aerosol jet of droplets at a temperature from about 20° C. to 150° C. when the flow rate of the liquid entering the capillary tube is from about 100 $\mu$L/minute to 2000 $\mu$L/minute;

(c) directing an annular jet of gas past said free end of said capillary tube in said chamber in the direction of flow of said liquid to nebulize said liquid;

(d) maintaining the pressure in said chamber at substantially atmospheric pressure;

(e) applying an electric field in said chamber between said free end and an orifice plate for said ions, the combination of said heating, said electric field and said nebulization acting to produce a mist of charged droplets and to produce ions from said droplets; said charged droplets having a predominance of singly charged ions relative to multiply-charged ions and having a single polarity, either positive or negative, the same as the polarity of the applied electric field; and (f) guiding said ions through said orifice into a mass analyzer located beyond said orifice.

22. The method according to claim 21 wherein the velocity of said jet of gas is in the range between about 140 and 250 meters per second.

23. The method according to claim 21 and including the step of pre-separating components of said liquid in a liquid chromatograph prior to directing said liquid through said capillary tube.

24. The method of claim 21 wherein the capillary tube is heated at a temperature from about 150° C. to about 170° C., the temperature of the aerosol jet is less than about 100° C. and the liquid flow rate is from about 500 to 1000 $\mu$L/minute.

* * * * *